(12) United States Patent
Maxson

(10) Patent No.: US 11,364,059 B2
(45) Date of Patent: Jun. 21, 2022

(54) PECTUS BAR SUPPORT DEVICES AND METHODS

(71) Applicant: Zimmer Biomet CMF and Thoracic, LLC, Jacksonville, FL (US)

(72) Inventor: William Maxson, Ponte Vedra, FL (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 102 days.

(21) Appl. No.: 16/804,325

(22) Filed: Feb. 28, 2020

(65) Prior Publication Data

US 2020/0197058 A1 Jun. 25, 2020

Related U.S. Application Data

(63) Continuation of application No. 15/892,487, filed on Feb. 9, 2018, now Pat. No. 10,617,455.

(60) Provisional application No. 62/468,690, filed on Mar. 8, 2017.

(51) Int. Cl.
*A61B 17/80* (2006.01)
(52) U.S. Cl.
CPC .................. *A61B 17/8076* (2013.01)
(58) Field of Classification Search
CPC . A61B 17/80; A61B 17/8061; A61B 17/8076; A61B 17/842
See application file for complete search history.

(56) References Cited

U.S. PATENT DOCUMENTS

| | | |
|---|---|---|
| 212,242 A | 2/1879 | Loper |
| 2,616,328 A | 11/1952 | Vincent |
| 3,946,728 A | 3/1976 | Bettex |
| 4,082,332 A | 4/1978 | Palmer |
| 4,201,215 A | 5/1980 | Crossett et al. |
| 4,202,327 A | 5/1980 | Glancy |
| 4,327,715 A | 5/1982 | Corvisier |
| 5,092,889 A | 3/1992 | Campbell, Jr. |
| 5,605,364 A | 2/1997 | Shelledy |

(Continued)

FOREIGN PATENT DOCUMENTS

| | | |
|---|---|---|
| CN | 101123922 A | 2/2008 |
| CN | 201930064 U | 8/2011 |

(Continued)

OTHER PUBLICATIONS

"U.S. Appl. No. 11/402,319, Advisory Action dated Oct. 13, 2009", 4 pgs.

(Continued)

*Primary Examiner* — Eric S Gibson
(74) *Attorney, Agent, or Firm* — Schwegman Lundberg & Woessner, P.A.

(57) ABSTRACT

A pectus bar assembly including a bar support and a pectus bar. The bar support can include a fastener and a fabric. A fabric can encircle a first rib and a second rib of a human ribcage. The fabric can include a first free end securable to the fastener and a second free end securable to the fastener to tension the fabric around the first rib and the second rib. The pectus bar can include an elongate body. The elongate body can include an anterior side and a posterior side opposite the anterior side. The posterior side can be supported by the bar support between the first rib and the second rib.

20 Claims, 10 Drawing Sheets

(56) References Cited

U.S. PATENT DOCUMENTS

| | | | |
|---|---|---|---|
| 5,755,808 | A | 5/1998 | Decarlo et al. |
| 6,005,018 | A | 12/1999 | Cicierega et al. |
| 6,007,538 | A | 12/1999 | Levin |
| 6,024,759 | A * | 2/2000 | Nuss ............... A61B 17/68 606/237 |
| 6,306,136 | B1 | 10/2001 | Baccelli |
| 6,355,038 | B1 | 3/2002 | Pisharodi |
| 6,656,179 | B1 | 12/2003 | Schaefer et al. |
| 6,689,134 | B2 | 2/2004 | Ralph et al. |
| 6,872,210 | B2 | 3/2005 | Hearn |
| 7,156,847 | B2 * | 1/2007 | Abramson ......... A61B 17/8076 606/60 |
| 7,601,165 | B2 | 10/2009 | Stone |
| 8,597,327 | B2 | 12/2013 | Stone et al. |
| 8,715,285 | B2 * | 5/2014 | Lewis ............. A61B 17/8076 606/71 |
| 8,876,823 | B2 * | 11/2014 | Li .................. A61B 17/8023 606/70 |
| 9,138,272 | B2 | 9/2015 | Roman et al. |
| 9,339,388 | B2 | 5/2016 | Dartevelle |
| 9,668,792 | B2 | 6/2017 | Roman et al. |
| 9,743,968 | B2 * | 8/2017 | Licht ............... A61B 17/8085 |
| 9,775,657 | B2 * | 10/2017 | Bernstein ........... A61B 17/808 |
| 9,833,269 | B2 * | 12/2017 | Park ................ A61B 17/8076 |
| 9,872,708 | B2 * | 1/2018 | Park ................ A61B 17/8869 |
| 10,058,364 | B2 * | 8/2018 | Garcia .............. A61B 17/823 |
| 10,617,455 | B2 * | 4/2020 | Maxson ............... A61B 17/68 |
| 10,722,279 | B2 | 7/2020 | Balzano et al. |
| 10,820,931 | B2 | 11/2020 | Garcia et al. |
| 2002/0143336 | A1 | 10/2002 | Hearn |
| 2003/0225409 | A1 | 12/2003 | Freid et al. |
| 2004/0030338 | A1 | 2/2004 | Paul |
| 2004/0116931 | A1 | 6/2004 | Carlson |
| 2004/0117016 | A1 * | 6/2004 | Abramson ......... A61B 17/8076 623/16.11 |
| 2004/0204713 | A1 | 10/2004 | Abdou |
| 2005/0049595 | A1 | 3/2005 | Suh et al. |
| 2006/0058786 | A1 * | 3/2006 | Kim ................ A61B 17/8076 606/60 |
| 2006/0089648 | A1 | 4/2006 | Masini |
| 2006/0259141 | A1 * | 11/2006 | Roman ............. A61B 17/8061 623/11.11 |
| 2008/0082101 | A1 * | 4/2008 | Reisberg ......... A61B 17/8076 606/60 |
| 2008/0097444 | A1 | 4/2008 | Erickson et al. |
| 2008/0262549 | A1 | 10/2008 | Bennett et al. |
| 2009/0062918 | A1 | 3/2009 | Wang et al. |
| 2010/0256691 | A1 * | 10/2010 | Park ............... A61B 17/8076 606/330 |
| 2011/0160776 | A1 | 6/2011 | Erickson et al. |
| 2011/0251540 | A1 * | 10/2011 | Notrica ........... A61B 17/8076 602/19 |
| 2012/0130371 | A1 * | 5/2012 | Li .................. A61B 17/8023 606/70 |
| 2012/0303121 | A1 * | 11/2012 | Douget ............. A61B 17/842 623/13.14 |
| 2013/0165934 | A1 | 6/2013 | Ibrahim et al. |
| 2013/0020431 | A1 | 8/2013 | Roman et al. |
| 2014/0117016 | A1 | 5/2014 | Hodge |
| 2014/0135853 | A1 * | 5/2014 | Reisberg ......... A61B 17/707 606/324 |
| 2014/0163691 | A1 * | 6/2014 | Dartevelle ....... A61B 17/8076 623/23.53 |
| 2014/0214103 | A1 | 7/2014 | Roman et al. |
| 2014/0309699 | A1 | 10/2014 | Houff |
| 2014/0378976 | A1 * | 12/2014 | Garcia ............ A61B 17/842 606/74 |
| 2015/0038969 | A1 | 2/2015 | Garcia et al. |
| 2015/0045794 | A1 | 2/2015 | Garcia et al. |
| 2015/0119887 | A1 | 4/2015 | May et al. |
| 2015/0134009 | A1 * | 5/2015 | Licht .............. A61B 17/8014 606/281 |
| 2015/0238237 | A1 * | 8/2015 | Madjarov ........... A61B 17/842 606/281 |
| 2016/0074078 | A1 | 3/2016 | Roman et al. |
| 2016/0296262 | A1 | 10/2016 | Garcia et al. |
| 2016/0310180 | A1 | 10/2016 | Prybis et al. |
| 2016/0367301 | A1 * | 12/2016 | Madjarov ......... A61B 17/8085 |
| 2017/0156759 | A1 * | 6/2017 | Park ................ A61B 17/8076 |
| 2017/0215930 | A1 | 8/2017 | Lauf et al. |
| 2017/0238981 | A1 * | 8/2017 | Madjarov ......... A61B 17/8085 |
| 2018/0228523 | A1 | 8/2018 | Balzano et al. |
| 2018/0228524 | A1 * | 8/2018 | Garcia ............ A61B 17/8875 |
| 2018/0256227 | A1 * | 9/2018 | Maxson ................ A61B 17/84 |
| 2018/0303527 | A1 * | 10/2018 | Su .................. A61B 17/8004 |
| 2018/0310973 | A1 * | 11/2018 | Son ................ A61B 17/8076 |
| 2018/0368896 | A1 * | 12/2018 | Powell ............ A61B 17/8076 |
| 2019/0046251 | A1 * | 2/2019 | Detweiler ........ A61B 17/8872 |
| 2019/0059964 | A1 * | 2/2019 | Notrica ........... A61B 17/8863 |
| 2019/0069938 | A1 * | 3/2019 | Martinez-Ferro ..................... A61B 17/8076 |
| 2019/0314072 | A1 * | 10/2019 | Uemura ............... A61B 17/86 |
| 2020/0197058 | A1 * | 6/2020 | Maxson ................ A61B 17/84 |
| 2020/0315676 | A1 | 10/2020 | Balzano et al. |
| 2021/0007785 | A1 | 1/2021 | Garcia et al. |

FOREIGN PATENT DOCUMENTS

| | | |
|---|---|---|
| CN | 203059880 U | 7/2013 |
| CN | 103767778 A | 5/2014 |
| CN | 104856748 A | 8/2015 |
| CN | 204683752 U | 10/2015 |
| CN | 110325135 A | 10/2019 |
| CN | 110366391 A | 10/2019 |
| EP | 0583520 A1 | 2/1994 |
| EP | 1721580 A1 | 11/2006 |
| JP | 2000501624 A | 2/2000 |
| JP | 2016168086 A | 9/2016 |
| JP | 2020508102 | 3/2020 |
| JP | 2020509827 | 4/2020 |
| WO | WO-2004028412 A1 | 4/2004 |
| WO | WO-2013003719 A1 | 1/2013 |
| WO | WO-2015003061 A1 | 1/2015 |
| WO | WO-2015056204 A1 | 4/2015 |
| WO | WO-2015142588 A2 | 9/2015 |
| WO | WO-2017023147 A1 | 2/2017 |
| WO | 2017157802 | 9/2017 |
| WO | WO-2018148521 A1 | 8/2018 |
| WO | WO-2018148572 A1 | 8/2018 |
| WO | WO-2018164808 A1 | 9/2018 |

OTHER PUBLICATIONS

"U.S. Appl. No. 11/402,319, Appeal Brief filed Jan. 4, 2010", 24 pgs.

"U.S. Appl. No. 11/402,319, Decision on Appeal dated Aug. 29, 2012", 9 pgs.

"U.S. Appl. No. 11/402,319, Examiner Interview Summary dated Apr. 6, 2009", 2 pgs.

"U.S. Appl. No. 11/402,319, Final Office Action dated Aug. 5, 2009", 11 pgs.

"U.S. Appl. No. 11/402,319, Non Final Office Action dated Feb. 23, 2009", 10 pgs.

"U.S. Appl. No. 11/402,319, Reply Brief filed Apr. 26, 2010", 6 pgs.

"U.S. Appl. No. 11/402,319, Reply Brief filed Jun. 2, 2010", 6 pgs.

"U.S. Appl. No. 11/402,319, Response filed Jan. 27, 2009 to Restriction Requirement dated Dec. 31, 2008", 3 pgs.

"U.S. Appl. No. 11/402,319, Response filed Apr. 8, 2009 to Non Final Office Action dated Feb. 23, 2009", 11 pgs.

"U.S. Appl. No. 11/402,319, Response filed Sep. 24, 2009 to Final Office Action dated Aug. 5, 2009", 7 pgs.

"U.S. Appl. No. 11/402,319, Restriction Requirement dated Dec. 31, 2008", 9 pgs.

"U.S. Appl. No. 13/662,975, Notice of Allowance dated Dec. 24, 2013", 9 pgs.

"U.S. Appl. No. 13/662,975, Preliminary Amendment filed Jul. 1, 2013", 11 pgs.

(56) References Cited

OTHER PUBLICATIONS

"U.S. Appl. No. 13/662,975, Response filed Sep. 30, 2013 to Restriction Requirement dated Aug. 28, 2013", 9 pgs.
"U.S. Appl. No. 13/662,975, Restriction Requirement dated Aug. 28, 2013", 9 pgs.
"U.S. Appl. No. 14/243,246, Notice of Allowance dated May 20, 2015", 9 pgs.
"Application Serial No. 14/531,US4, Response filed Jan. 12, 2017 to Final Office Action dated Dec. 7, 2016", 9 pgs.
"U.S. Appl. No. 14/857,422, Final Office Action dated Dec. 7, 2016", 12 pgs.
"U.S. Appl. No. 14/857,422, Non Final Office Action dated Apr. 19, 2016", 5 pgs.
"U.S. Appl. No. 14/857,422, Notice of Allowance dated Jan. 25, 2017", 7 pgs.
"U.S. Appl. No. 14/857,422, Response filed Sep. 19, 2016 to Non Final Office Action dated Apr. 19, 2016", 8 pgs.
"U.S. Appl. No. 15/892,847, Notice of Allowance dated Nov. 29, 2019", 10 pgs.
"U.S. Appl. No. 15/892,926, Non Final Office Action dated Nov. 29, 2019", 15 pgs.
"U.S. Appl. No. 15/892,926, Response filed Feb. 19, 2020 to Non Final Office Action dated Nov. 29, 2019", 11 pgs.
"U.S. Appl. No. 15/893,271, Non Final Office Action dated Dec. 27, 2019", 12 pgs.
"Australian Application Serial No. 2018217805, First Examination Report dated Nov. 25, 2019", 4 pgs.
"European Application Serial No. 06009368.9, Communication Pursuant to Article 94(3) EPC dated Mar. 1, 2017", 5 pgs.
"European Application Serial No. 06009368.9, Communication Pursuant to Article 94(3) EPC dated Oct. 8, 2015", 4 pgs.
"European Application Serial No. 06009368.9, Extended European Search Report dated Sep. 15, 2006", 11 pgs.
"European Application Serial No. 06009368.9, Office Action dated Jun. 14, 2007", 1 pg.
"European Application Serial No. 06009368.9, Response filed Apr. 18, 2016 to Communication Pursuant to Article 94(3) EPC dated Oct. 8, 2015", 15 pgs.
"European Application Serial No. 06009368.9, Response filed Sep. 11, 2017 to Communication Pursuant to Article 94(3) EPC dated Mar. 1, 2017", 24 pgs.
"European Application Serial No. 06009368.9, Response filed Dec. 24, 2007 to Office Action dated Jun. 14, 2007", 11 pgs.
"International Application Serial No. PCT/US2018/017582, International Preliminary Report on Patentability dated Sep. 19, 2019", 9 pgs.
"International Application Serial No. PCT/US2018/017582, International Search Report dated May 16, 2018", 7 pgs.
"International Application Serial No. PCT/US2018/017582, Written Opinion dated May 16, 2018", 7 pgs.
"International Application Serial No. PCT/US2018/017591, International Preliminary Report on Patentability dated Aug. 22, 2019", 11 pgs.
"International Application Serial No. PCT/US2018/017591, International Search Report dated Apr. 25, 2018", 7 pgs.
"International Application Serial No. PCT/US2018/017591, Written Opinion dated Apr. 25, 2018", 9 pgs.
"International Application Serial No. PCT/US2018/017663, International Preliminary Report on Patentability dated Aug. 22, 2019", 18 pgs.
"International Application Serial No. PCT/US2018/017663, International Search Report dated Jun. 18, 2018", 10 pgs.
"International Application Serial No. PCT/US2018/017663, Invitation to Pay Add'l Fees and Partial Search Report dated Apr. 23, 2018", 21 pgs.
"International Application Serial No. PCT/US2018/017663, Written Opinion dated Jun. 18, 2018", 16 pgs.
"U.S. Appl. No. 15/892,926, Notice of Allowance dated Mar. 23, 2020", 11 pgs.
"U.S. Appl. No. 15/893,271, Response filed Mar. 18, 2020 to Non Final Office Action dated Dec. 27, 2019", 13 pgs.
"Australian Application Serial No. 2018217805, Response filed Feb. 25, 2020 First Examination Report dated Nov. 25, 2019", 25 pgs.
"Australian Application Serial No. 2018230818, First Examination Report dated Feb. 19, 2020", 5 pgs.
"European Application Serial No. 18707802.7, Response to Communication pursuant to Rules 161(1) and 162 EPC filed Mar. 30, 2020", 11 pages.
"European Application Serial No. 18707204.6, Response to Communication pursuant to Rules 161(1) and 162 EPC filed Mar. 30, 2020", 17 pages.
"Australian Application Serial No. 2018230818, Response filed May 5, 2020 to First Examination Report dated Feb. 19, 2020", 23 pages.
"European Application Serial No. 18706624.6, Response to Communication pursuant to Rules 161(1) and 162 EPC filed May 5, 2020", 11 pages.
"Australian Application Serial No. 2018230818, Subsequent Examiners Report dated May 28, 2020", 5 pages.
"U.S. Appl. No. 15/893,271, Notice of Allowance dated Jun. 29, 2020", 11 pgs.
"U.S. Appl. No. 16/908,188, Non Final Office Action dated Feb. 1, 2022", 16 pgs.
"U.S. Appl. No. 16/908,188, Preliminary Amendment filed Jun. 25, 2020", 7 pages.
"U.S. Appl. No. 17/034,697 Supplemental Preliminary Amendment filed Feb. 21, 2022", 6 pgs.
"U.S. Appl. No. 17/034,697, Preliminary Amendment filed Sep. 29, 2020", 6 pgs.
"Australian Application Serial No. 2018230818, Response filed Aug. 28, 2020 to Subsequent Examiners Report dated May 28, 2020", 17 pgs.
"Australian Application Serial No. 2018230818, Response filed Nov. 20, 2020 to Subsequent Examiners Report dated May 28, 2020", 11 pgs.
"Australian Application Serial No. 2018230818, Subsequent Examiners Report dated Sep. 21, 2020", 4 pgs.
"Canadian Application Serial No. 3,053,113, Office Action dated May 31, 2021", 5 pgs.
"Canadian Application Serial No. 3,053,113, Office Action dated Sep. 25, 2020", 4 pgs.
"Canadian Application Serial No. 3,053,113, Response filed Sep. 29, 2021 to Office Action dated May 31, 2021", 20 pgs.
"Canadian Application Serial No. 3,053,113, Response to Office Action dated Sep. 25, 2020", 29 pgs.
"Canadian Application Serial No. 3,054,790, Office Action dated Nov. 12, 2020", 4 pgs.
"Canadian Application Serial No. 3,054,790, Response filed Mar. 12, 2021 to Office Action dated Nov. 12, 2020", 13 pgs.
"Chinese Application Serial No. 201880011148.1, Office Action dated Feb. 14, 2022", w/ English Translation, 18 pgs.
"Chinese Application Serial No. 201880011148.1, Response filed Jan. 4, 2022 to Notification of Paying the Restoration Fee dated Nov. 18, 2021", w/ Claims, 6 pgs.
"Chinese Application Serial No. 201880014508.3, Office Action dated Nov. 17, 2021", w/ English translation, 9 pgs.
"Chinese Application Serial No. 201880014508.3, Response filed Feb. 23, 2022 to Office Action dated Nov. 17, 2021", w/ English claims, 10 pgs.
"European Application Serial No. 18707204.6, Communication Pursuant to Article 94(3) EPC dated Mar. 16, 2022", 8 pgs.
"Japanese Application Serial No. 2019-543354, Notification of Reasons for Refusal dated Jan. 5, 2021", (W/ English Translation), 11 pgs.
"Japanese Application Serial No. 2019-543354, Notification of Reasons for Refusal dated Dec. 7, 2021", w/ English translation, 8 pgs.
"Japanese Application Serial No. 2019-543354, Response filed Mar. 7, 2022 to Notification of Reasons for Refusal dated Dec. 7, 2021", w/English Claims, 15 pgs.

(56) References Cited

OTHER PUBLICATIONS

"Japanese Application Serial No. 2019-543354, Response filed Jun. 30, 2021 to Notification of Reasons for Refusal dated Jan. 5, 2021", w/ English claims, 13 pgs.

"Japanese Application Serial No. 2019-548548, Notification of Reasons for Refusal dated Jan. 5, 2021", (W/ English Translation), 10 pgs.

"Japanese Application Serial No. 2019-548548, Response filed Apr. 5, 2021 to Notification of Reasons for Refusal dated Jan. 5, 2021", w/ English claim, 10 pgs.

\* cited by examiner

PECTUS BAR SUPPORT DEVICES AND METHODS

CLAIM OF PRIORITY

This application is a continuation of U.S. patent application Ser. No. 15/892,847, filed on Feb. 9, 2018, which claims the benefit of U.S. Provisional Patent Application Ser. No. 62/468,690, filed on Mar. 8, 2017, the benefit of priority of each of which is claimed hereby, and each of which is incorporated by, reference herein in its entirety.

BACKGROUND

Pectus excavatum is a condition affecting a human rib cage which can result from a congenital disorder or injury. In some cases of pectus excavatum, physicians install hardware into a patient's ribcage to reshape the ribcage. Depending on the anatomy of the patient, current hardware solutions may be difficult to secure to a patient and to other hardware. Further, some solutions include devices that may require significant manual labor to properly install.

Overview

In cases where pectus excavatum requires surgical correction, a common corrective procedure includes securing a pectus bar to a patient's rib cage to reshape and stabilize the rib cage. This procedure can include the steps of: creating opposing incisions on each side of a patient's rib cage; inserting a curved pectus bar into one of the incisions; weaving the pectus bar through one or more ribs; flipping the pectus bar; securing the pectus bar to the rib cage; and, closing the incisions.

In some of these surgical procedures, support of the pectus bar may be helpful to ensure the bar maintains its position within the ribcage and reduce the likelihood of structural damage to the ribcage or discomfort for the patient. In some of these cases, it may not be possible to secure stabilizer hardware to the pectus bar to provide support to the pectus bar. The inventors have recognized, among other things, that in such cases, a bar support may be secured between two ribs to provide support for the bar.

To further illustrate the apparatuses and systems disclosed herein, the following non-limiting examples are provided:

Example 1 is a pectus bar assembly comprising: a bar support comprising: a fastener; and a fabric configured to encircle a first rib and a second rib of a human ribcage, the fabric comprising: a first free end securable to the fastener; and a second free end securable to the fastener to tension the fabric around the first rib and the second rib; and a pectus bar comprising an elongate body, the elongate body comprising: an anterior side; and a posterior side opposite the anterior side, the posterior side supportable by the bar support between the first rib and the second rib.

In Example 2, the subject matter of Example 1 optionally includes the fastener comprising: a base; and an insert threadably coupleable to the base.

In Example 3, the subject matter of Example 2 optionally includes wherein the insert is operable to compress the first free end and the second free end to the base to secure the fabric to the fastener.

In Example 4, the subject matter of Example 3 optionally includes the base further comprising: a threaded bore structured to threadably engage the insert.

In Example 5, the subject matter of Example 4 optionally includes the base further comprising: a slot extending from the threaded bore to a periphery of the base, the slot configured to receive the first free end and the second free end.

In Example 6, the subject matter of any one or more of Examples 1-5 optionally include wherein the fabric is comprised of at least one of polyethylene, polyester, polyamide, a titanium alloy, and a stainless steel alloy.

In Example 7, the subject matter of any one or more of Examples 1-6 optionally include a second bar support configured to be coupled to the first rib and the second rib, the second bar support structured for supporting the pectus bar.

Example 8 is a pectus bar assembly comprising: a bar support comprising: a first portion sized to encircle a first rib of a human ribcage; a second portion connected to the first portion, the second portion sized to encircle a second rib of the human ribcage adjacent to the first rib; and first and second free ends, at least one of which is adjustable to tension the first portion and the second portion around the first rib and the second rib, respectively; and a pectus bar comprising an elongate body, the elongate body comprising: an anterior side; and a posterior side opposite the anterior side, the posterior side configured to be supported by the bar support between the first rib and the second rib.

In Example 9, the subject matter of Example 8 optionally includes the bar support further comprising: a connector secured to the first portion and the second portion.

In Example 10, the subject matter of Example 9 optionally includes wherein the first portion is releasably coupled to the connector.

In Example 11, the subject matter of any one or more of Examples 9-10 optionally include the connector further comprising: an open end configured to releasably secure the first portion to the connector.

In Example 12, the subject matter of any one or more of Examples 8-11 optionally include the bar support further comprising: a sleeve coupled to the first portion and the second portion, the first free end and the second free end passing through the sleeve to create at least one loop.

In Example 13, the subject matter of any one or more of Examples 8-12 optionally include a second bar support configured to be coupled to the first rib and the second rib, the second bar support structured for supporting the pectus bar.

Example 14 is a pectus bar assembly comprising: a bar support comprising: a band configured to encircle a first rib of a human ribcage and a second rib of the human ribcage, the band comprising a first end and a second end opposite the first end; a fastener coupleable to the first end, the second end releasably securable to the fastener to tension the band around the first rib and the second rib; and a pectus bar comprising an elongate body, the elongate body comprising: an anterior side; and a posterior side opposite the anterior side, the posterior side supportable by the bar support between the first rib and the second rib.

In Example 15, the subject matter of Example 14 optionally includes wherein the fastener comprises: a buckle extending from the second end.

In Example 16, the subject matter of Example 15 optionally includes the buckle further comprising: an aperture configured to receive the first end; and a cam rotatable within the buckle to secure the first end to the buckle:

In Example 17, the subject matter of any one or more of Examples 14-16 optionally include the band further comprising a slot configured to receive the pectus bar there through.

In Example 18, the subject matter of any one or more of Examples 14-17 optionally include the second head further comprising: a second bar support configured to be coupled to the first rib and the second rib, the second bar support structured for supporting the pectus bar.

In Example 19, the subject matter of Example 18 optionally includes wherein the bar support is configured to support the posterior side of the pectus bar and wherein the second bar support is configured to support the anterior side of the pectus bar.

In Example 20, the subject matter of Example 19 optionally includes wherein the band is comprised of at least one of a titanium alloy and a stainless steel alloy.

Example 21 is a method of securing a pectus bar to a human ribcage, the method comprising: positioning a pectus bar in a human rib cage; securing a first portion of a support to a first rib; securing a second portion of the support to a second rib; and supporting a posterior portion of the pectus bar with the support.

In Example 22, the subject matter of Example 21 optionally includes adjusting a tension of the support.

In Example 23, the subject matter of any one or more of Examples 21-22 optionally include inserting a first end of the support into a fastener; inserting a second end of the support into the fastener; and securing the first end and the second end with the fastener.

In Example 24, the subject matter of any one or more of Examples 21-23 optionally include inserting a second end of the support into a fastener coupled to the first end; and securing the first end to the second end with the fastener.

In Example 25, the subject matter of any one or more of Examples 21-24 optionally include securing a second end of the support to a loop coupled to the first end; and adjusting a first free end and a second free end of the support to secure the second end to the loop.

In Example 26, the pectus bar stabilizer insertion tool, assembly, or method of any one of or any combination of Examples 1-25 is optionally configured such that all elements or options recited are available to use or select from.

These and other examples and features of the present apparatuses and systems will be set forth in part in the following Detailed Description. This Overview is intended to provide non-limiting examples of the present subject matter and it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to devices and systems for sternal correction. For example, the present application discloses an assembly for coupling a pectus bar and stabilizers to a rib cage of a patient to correct pectus excavatum.

Figure 1:
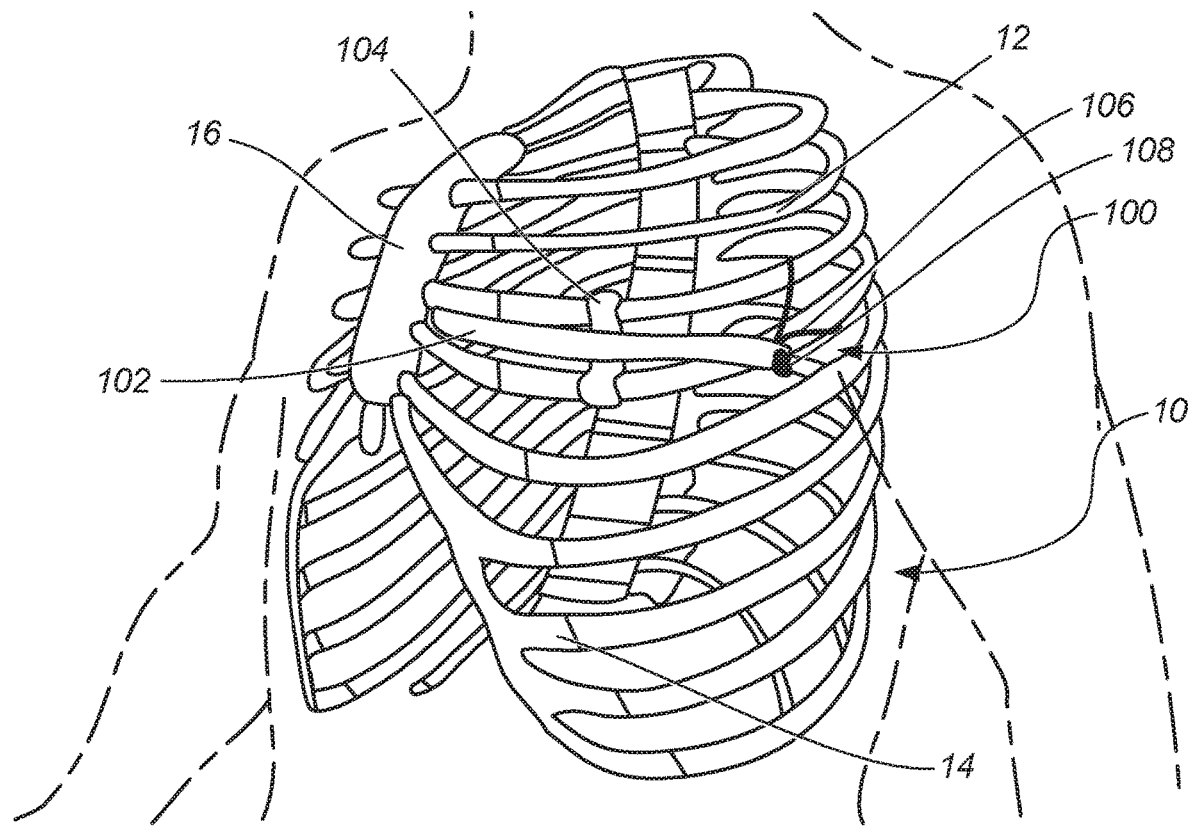
FIG. 1 illustrates an isometric view of a pectus bar assembly installed in a ribcage of a patient, in accordance with at least one example of the present disclosure.

FIG. 1 illustrates an isometric view of pectus bar assembly 100, which can include pectus bar 102, bar support 104, and bar tie 106. Pectus bar 102 can include one or more bar bores 108 (only one shown in FIG. 1). Also shown in FIG. 1 is ribcage 10, which can include ribs 12, costal cartilage 14, and sternum 16.

Pectus bar 102 can be a rigid or semi-rigid bar constructed of materials such as metals and plastics. Pectus bar 102 can have an elongate body forming a curve, such as a c-shape, in some examples. Bar bores 108 can be disposed near the terminations of pectus bar 102 and can be configured to receive fasteners, such as bone screws or sutures, to secure pectus bar 102 to ribs and/or soft tissues (such as cartilage) of a patient.

Bar support 104 can be a semi-rigid or flexible component constructed of materials such as metals and plastics. Bar support 104 can be configured to engage and secure to ribs 12, more specifically between two adjacent ribs 12 of ribcage 10. Bar support 104 can be tensioned between ribs 12 to provide support for pectus bar 102 anywhere along the length of pectus bar 102. Bar support 104 can also include a locking mechanism (shown and discussed below) that can be used to secure bar support 104 to itself.

In operation of some examples, a procedure to correct pectus excavatum can include creating opposing incisions on each side of a patient's rib cage and inserting pectus bar 102 into one of the incisions. Pectus bar 102 can then be weaved through one or more ribs of the patient and flipped into a final position. Either prior to or after insertion of pectus bar 102, bar support 104 can be inserted into one of the incisions and secured to two adjacent ribs 12 of rib cage 10. Pectus bar 102 can then be positioned so that pectus bar 102 is supported by bar support 104. Pectus bar 102 can be secured to the ribcage using bar bore 108 and bar tie 106 before final preparations are made and incisions are closed. During this process, a physician can position bar support 104 along the length of ribs 12 as desired.

In some cases of prior art, pectus bars may tear through intra-costal muscle or other intra-costal tissues when the pectus bar becomes displaced within a patient's ribcage following a procedure. In some cases, ribs of the patient's rib cage can splay apart and/or the pectus bar can migrate inward (posteriorly), which can be problematic. The present disclosure addresses these issues by providing support to pectus bar 102. In doing so, bar support 104 can support pectus bar 102 and prevent inward movement of pectus bar 102, which can also prevent tearing of surrounding tissues. Bar support 104 can also prevent splaying of ribs, which can improve patient quality of life.

In some examples, placement of bar support 104 relative to ribs 12 can be of importance. By placing bar support 104 between skin and a chest wall and by locating bar support 104 adjacent to where pectus bar 102 exits muscle (through a muscle incision), bar support 104 can support pectus bar 102 at the highest stress point of pectus bar 102. This can help to minimize movement and deformation of pectus bar 102.

Also, bar support 104 can enable a physician to place and secure pectus bar 102 within a ribcage where other supporting hardware may be difficult to install or may be very palpable for a patient and therefore unaesthetic and/or uncomfortable. In these cases, bar support 104 can provide support to pectus bar 102 to prevent tissue damage and maintain positioning of pectus bar 102 within ribcage 10. Details of the components of pectus bar assembly 100 shown in FIG. 1 are discussed in further detail below.

Figure 2:
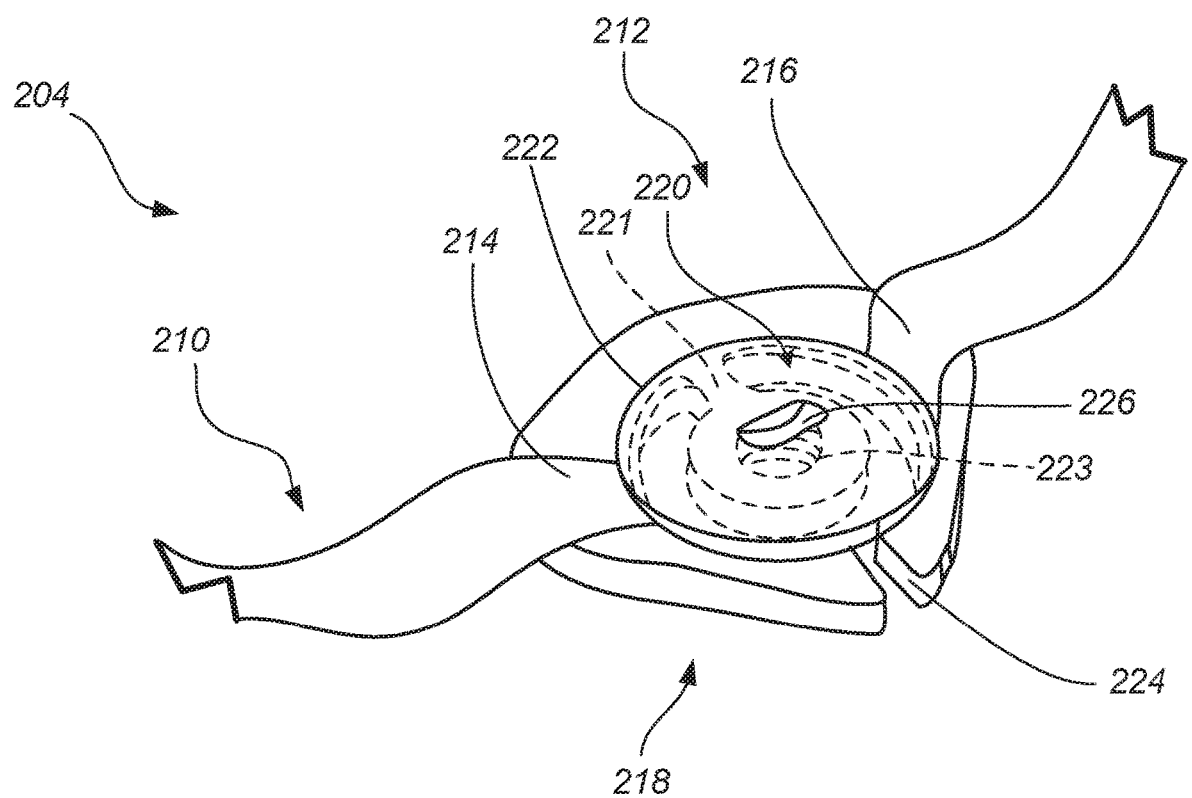
FIG. 2 illustrates an isometric view of a bar stabilizer, in accordance with at least one example of the present disclosure.

FIG. 2 illustrates an isometric view of bar stabilizer 204, which can include fabric 210 and fastener 212. Fabric 210 can include first end 214 and second end 216. Fastener 212 can include base 218 and insert 220. Base 218 can include extension 221. (including threaded bore 223), bore 222, and slot 224. Insert 220 can include slot 226.

Fabric 210 can be a flexible or semi-rigid member comprised of a material that is mesh, woven, braided, and the like. In some examples, fabric 210 can be comprised of polyethylene, polyester, polyamide, a titanium alloy, a stainless steel alloy, and the like. Fabric 210 can have a band-like or ribbon-like geometry, having a length significantly greater than a width and a thickness significantly smaller than the width. First end 214 can be a termination of fabric 210, which can be opposite second end 216 (a second termination of fabric 210).

Fastener 212 can be comprised of a rigid material, such as at least one plastic one metal, or a combination thereof. For example, fastener 212 can be comprised of biocompatible materials, such as stainless steel alloys, titanium alloys, cobalt-chromium alloys, and the like. Base 218 can have a geometric shape suitable to reduce palpability once installed in a patient. For example, base 218 can be contoured with eased edges. In some example, base 218 can be substantially circular or oval. In some other examples, base 218 can have an irregular shape.

Base 218 can include bore 222, which can be sized to receive insert 220. Extension 221 can extend radially inward from an internal diameter of bore 222 to define threaded bore 223 proximate a center of bore 222. Insert 220 can be threadably coupleable with threaded bore 223 of extension 221. Insert 220 can include slot 226, which can be sized to receive a tool for applying a torque to insert 220. Slot 224 can be a slot intersecting bore 222 and extending radially therefrom to an outer periphery of base 218, so that slot 224 (and therefore bore 222) is open to the perimeter of base 218. In some examples, fabric 210 can have a width that is smaller than a diameter of bore 222.

In operation of some examples, bar support 204 can be attached to ribs of the rib cage either before or after a pectus bar has been installed into a rib cage, such as ribcage 10 of FIG. 1. In one example, first end 214 can be wrapped around a first rib and second end 216 can be wrapped around a second, adjacent, rib. With insert 212 removed from bore 222, first end 214 and second end 216 can be inserted into bore 222. Insert 212 can then be threaded into threaded bore 223, moving an outer diameter of insert 212 into bore 222 and compressing first end 214 and second end 216 between the outer diameter of insert 212 and an inner diameter of bore 222, such that first end 214 and second end 216 are not free to move relative to base 218 once insert 220 is tightly threaded into threaded bore 223. First end 214 and second end 216 can be tensioned around the ribs, as desired, before insert 212 is secured to threaded bore 223.

In some examples, insert 220 can be partially secured to threaded bore 221 before first end 214 and second end 216 are inserted into bore 222. In some of these examples, after insert 220 is partially threaded, first end 214 and second end 216 can be inserted into bore 222 through slot 224 and positioned within bore 222 across from each other (so that first end 214 is diametrically opposing second end 216). Insert 220 can then be threaded into threaded bore 221 to secure insert 220 into base 218.

In some examples, first end 214 and second end 216 can be connected so that fabric 210 is one piece when inserted into bore 220. Once insert 212 is secured within bore 222, excess fabric can be trimmed between first end 214 and second end 216.

After first end 214 and second end 216 are secured to base 218 by insert 220, bar support 204 can support a pectus bar between two ribs, as shown in FIG. 1. In some examples, fastener 212 can be located on an anterior side of bar support 204 so that the pectus bar engages a consistent portion of fabric 210. In other examples, base 218 can be configured to engage and/or secure to the pectus bar on an anterior side of bar support 204.

In some examples, after bar support 204 has been installed onto ribs, bar support 204 may be removed by unscrewing insert 220 from threaded bore 221, allowing first end 214 and/or second end 216 to be removed from bore 222. Bar support 204 may be entirely removed from the ribcage or bar support 204 may be moved to another location to support the pectus bar. In some examples, fabric 210 may be loosened or tightened to better support the pectus bar. By providing a bar support that can be relatively easily installed, removed, and adjusted, bar support 204 can increase procedural efficiency, saving time and cost.

Figure 3:
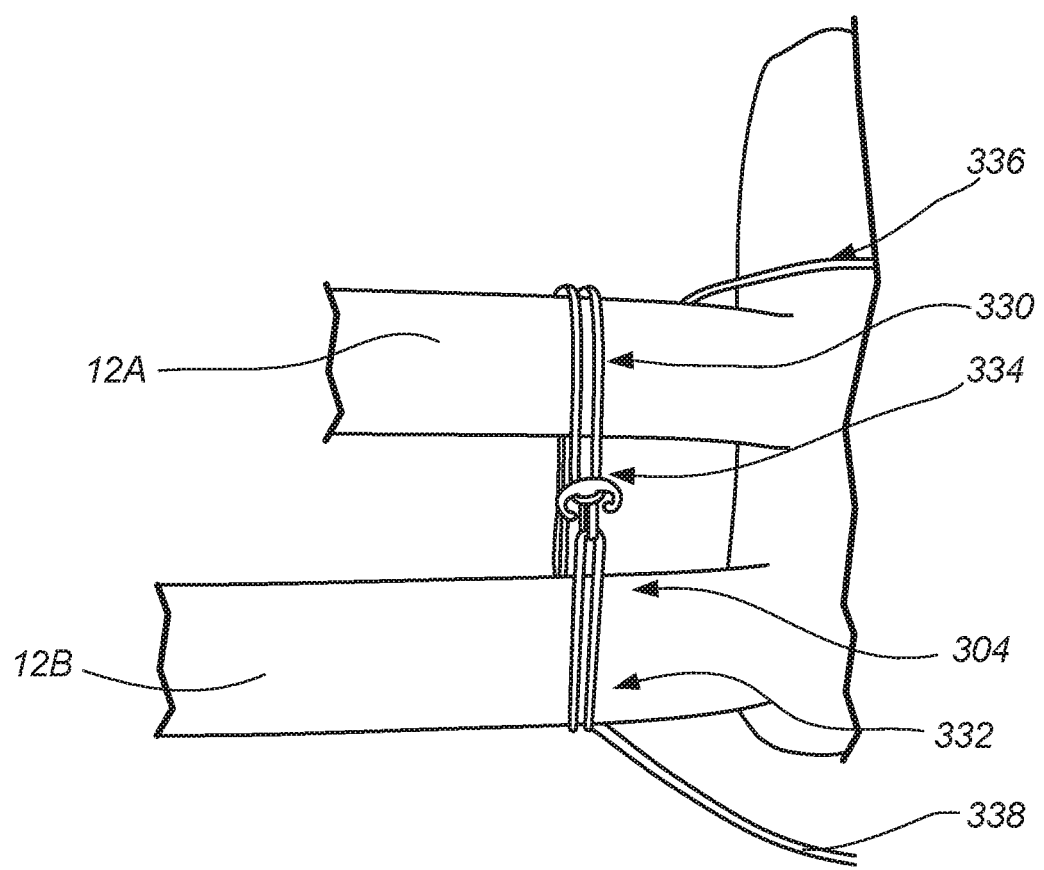
FIG. 3 illustrates an isometric view of a bar support installed on ribs, in accordance with at least one example of the present disclosure.

FIG. 3 illustrates an isometric view of bar support 304, which is another example of a bar support in accordance with the present disclosure. Bar support 304 can include first portion 330, second portion 332, coupler 334, first free end 336, and second free end 338. Also shown in FIG. 3 are ribs 12A and 12B.

First portion 330, second portion 332, first free end 336, and second free end 338 can be an assembly comprised of suture-like material, such as polyethylene, nylon, polyester, polypropylene, metallic strands, and the like. First portion 330 can be connected to second portion 332, First free end 336 and second free end 338 can be connected to first portion 330 and second portion 332, such that first free end 336, second free end 338, first portion 330, and second portion 332 are all coupled to each other.

Figure 4:
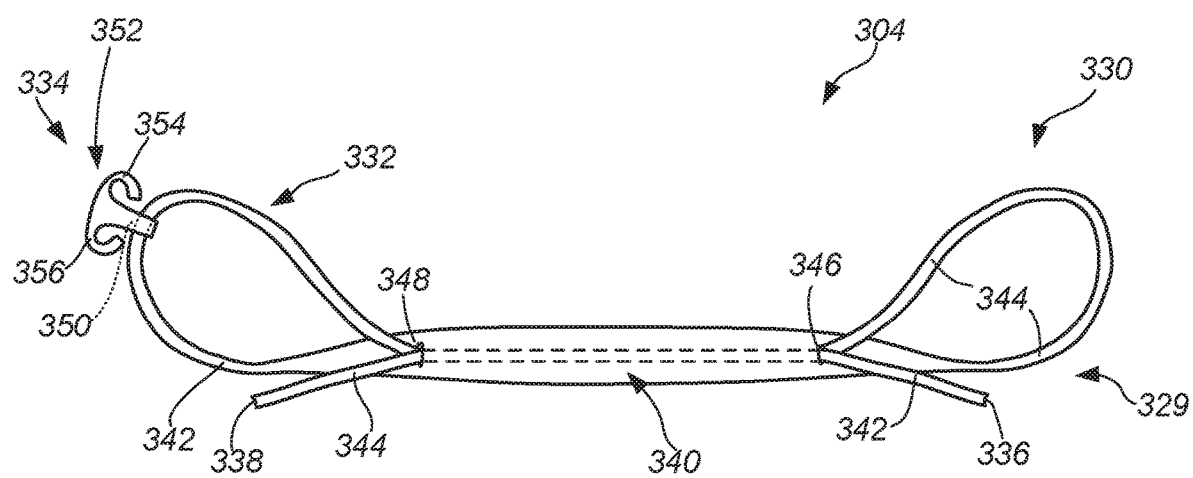
FIG. 4 illustrates a plan view of a bar support, in accordance with at least one example of the present disclosure.

Coupler 334 can be a rigid coupler or fastener comprised of biocompatible materials, such as plastics, metals, and the like. Coupler 334 can include a closed connector on one side and an open connector on a second side, as shown in FIG. 4.

In operation of some examples, bar support 304 can be secured to ribs 12A and 12B either before or after a pectus bar is inserted into a ribcage. Prior to the procedure, second portion 332 can be securely coupled to coupler 334. To connect bar support 304 to ribs 12A and 12B, second portion 332 can be positioned to encircle second rib 12B. Then, first portion 330 can be positioned to encircle first rib 12A and can then be releasably coupled to an open side of coupler 334. As a result, first free end 336 and second free end 338 can be loose portions of bar support 304. First free end 336 and/or second free end 338 can be pulled in opposing directions to tighten bar support 304 around ribs 12A and 12B and excess portions of first free end 336 and second free end 338 can be removed (trimmed), in some examples. Bar support 304 can be tensioned as desired to provide support for a pectus bar between ribs 12A and 12B. Further details of bar support 304 are discussed in FIG. 4 below, FIG. 4 illustrates plan view of bar support 304, which can include loop portion 329 and coupler 334. Loop portion 329 can include first portion 330, second portion 332, first free end 336, second free end 338, sleeve 340, strand 342, and strand 344. Sleeve 340 can include first opening 346 and second opening 348. Coupler 334 can include channel 350 and open end 352. Open end 352 can include first hook 354 and second hook 356.

Strand 342 and strand 344 can be connected to each other and connected to sleeve 340. Sleeve 340 can be a pocket or enclosure integral to loop portion 329 together with first strand 342 and second strand 344. Sleeve 340 can include first opening 346 proximate first portion 330 and second opening 348 proximate second portion 332. Sleeve 340 can be sized to receive one or more passes of both of strand 342 and strand 344, as discussed further below.

Coupler 334 can be a rigid coupler or fastener comprised of biocompatible materials, as described above. Coupler 334 can have a generally double-J-hook geometry with J-hooks facing substantially away from each other. Coupler 334 can include channel 350, which can be a passage or aperture disposed at the long portion of coupler 334 (or the closed portion), in some examples. Open end 352 of coupler 334 can include first hook 354 and second hook 356, each having an opening facing channel 350 and each being closed at a portion distal from channel 350. In other examples, coupler 334 can have other geometric shapes, such as a single J-hook, or coupler 334 can include a clasping device, such as a shackle or pivoting latch.

In assembly of one example of bar support 304, strand 342 can loop from second portion 332 through channel 350 of coupler 334, through second opening 348, through sleeve 340, and out first opening 348, terminating as first free end 336. Similarly, strand 344 can form a loop proximate first portion 330 and can enter first opening 346, pass through sleeve 340, and exit second opening 348, terminating as second free end 338. This assembly can be performed at a factory, or prior to a surgical procedure, to save time and cost.

Once bar support 304 is assembled as shown in FIG. 4, bar support 304 can be installed on ribs, as described above, where coupler 334 is moved to second portion 332 and is placed to encircle a second rib. First portion 330, either before or after coupler 334 and second portion encircle the second rib, can be placed to encircle a first rib. Then, strand 344 can be inserted into the openings of open end 352 into first hook 354 and second hook 356, respectively. Once strand 344 is installed to engage coupler 334, first free end and/or second free end can be pulled to tighten bar support 304 around the ribs, creating a support for a pectus bar. If desired, bar support 304 can be loosened and moved along the ribs, or can be removed and installed in another location, such as between two different ribs.

Bar support 304 can be quickly removed by cutting of either or both of strands 342 and 344. Because bar support 304 can be quickly installed, adjusted, and removed, bar support 304 can save time and cost in a procedure to install a pectus bar. Also, because strands 342 and 344 can be comprised of a relatively thin material, bar support 304 can lay relatively flat on ribs 12A and 12B, which can reduce palpability and can reduce irritation of surrounding tissues.

Figure 5:
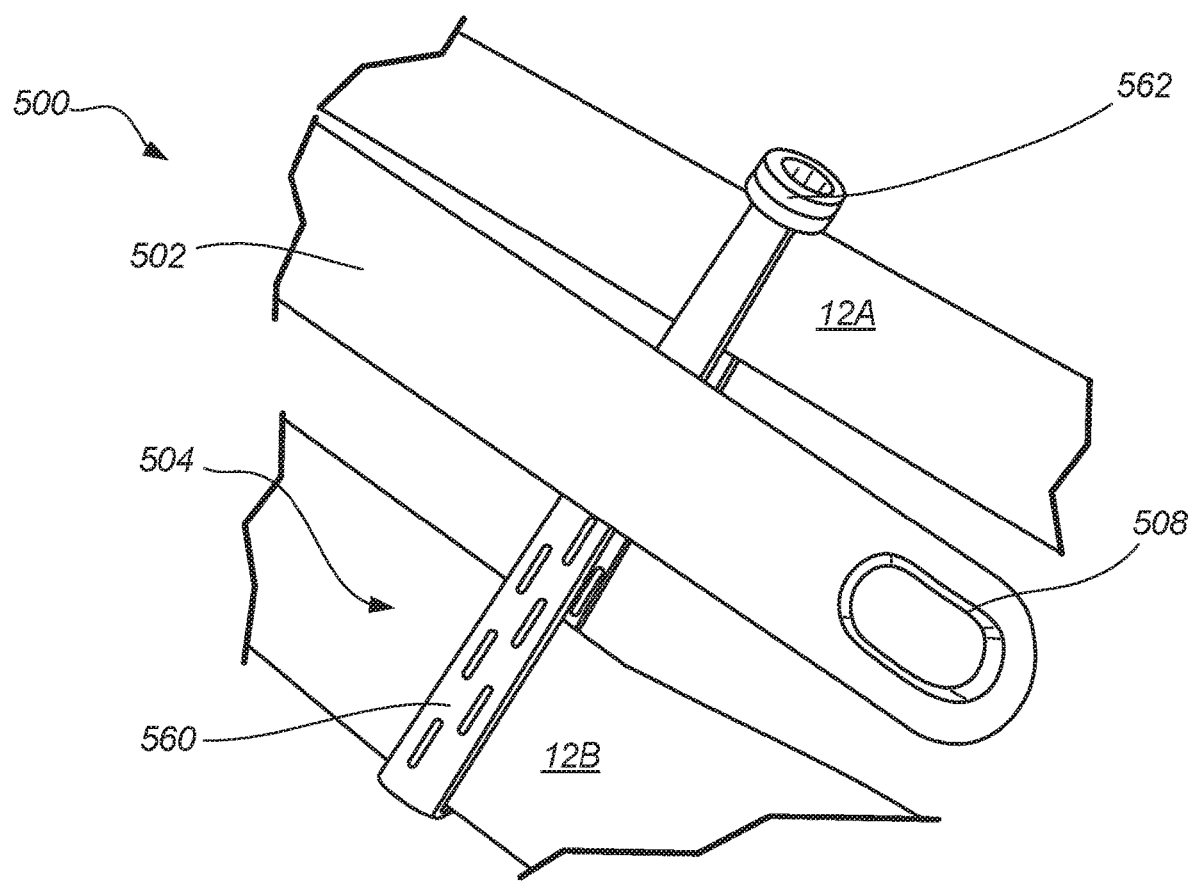
FIG. 5 illustrates an isometric view of a pectus bar band installed on ribs, in accordance with at least one example of the present disclosure.

FIG. 5 illustrates an isometric view of pectus bar assembly 500, which is another example of a pectus bar assembly in accordance with the present disclosure. Pectus bar assembly 500 can include pectus bar 502 (including bore 508) and bar support 504. Bar support 504 can include band 560 and fastener 562. Also shown in FIG. 5 are first rib 12A and second rib 12B.

Band 560 and fastener 562 can be comprised of biocompatible materials, such as plastics, stainless steel alloys, titanium alloys, and the like. Band 560 can have a band-like or ribbon-like geometry, having a length significantly greater than a width and a thickness significantly smaller than the width. Accordingly, band 560 can be flexible in directions substantially orthogonal to a plane defined by the length and width of band 560.

Fastener 562 can be coupled to one termination of band 560 and can be configured to receive another termination of band 560. Fastener 560 can be a simple fastening device, such as a clamp, in some examples, and can be a more complex fastening device, such as an aperture and cam system, as described in the example of FIG. 6 below.

In installation of some examples, band 560 can be positioned about first rib 12A and second rib 12B, as desired, and can be wrapped around second rib 12B and first rib 12A. Band 560 can couple to fastener 562 adjacent rib 12A, in some examples. Band 560 can then be repositioned about ribs 12A and 12B, as desired. Alternatively, band 560 can be removed from fastener 562 and removed from ribs 12A and 12B completely to be repositioned.

Once band 560 is deemed to be in an acceptable position, band 560 can be secured to fastener 560 at a desired tightness of band 560. Once coupled to fastener 562, excess portion of band 560 can be removed and pectus bar 502 can be placed between ribs 12A and 12B to be supported bar support 504. In some examples, multiple of bar supports 504 can be installed. Because bar support 504 can be quickly installed, adjusted, and removed, bar support 504 can save time and cost in a procedure to install a pectus bar.

Figure 6:
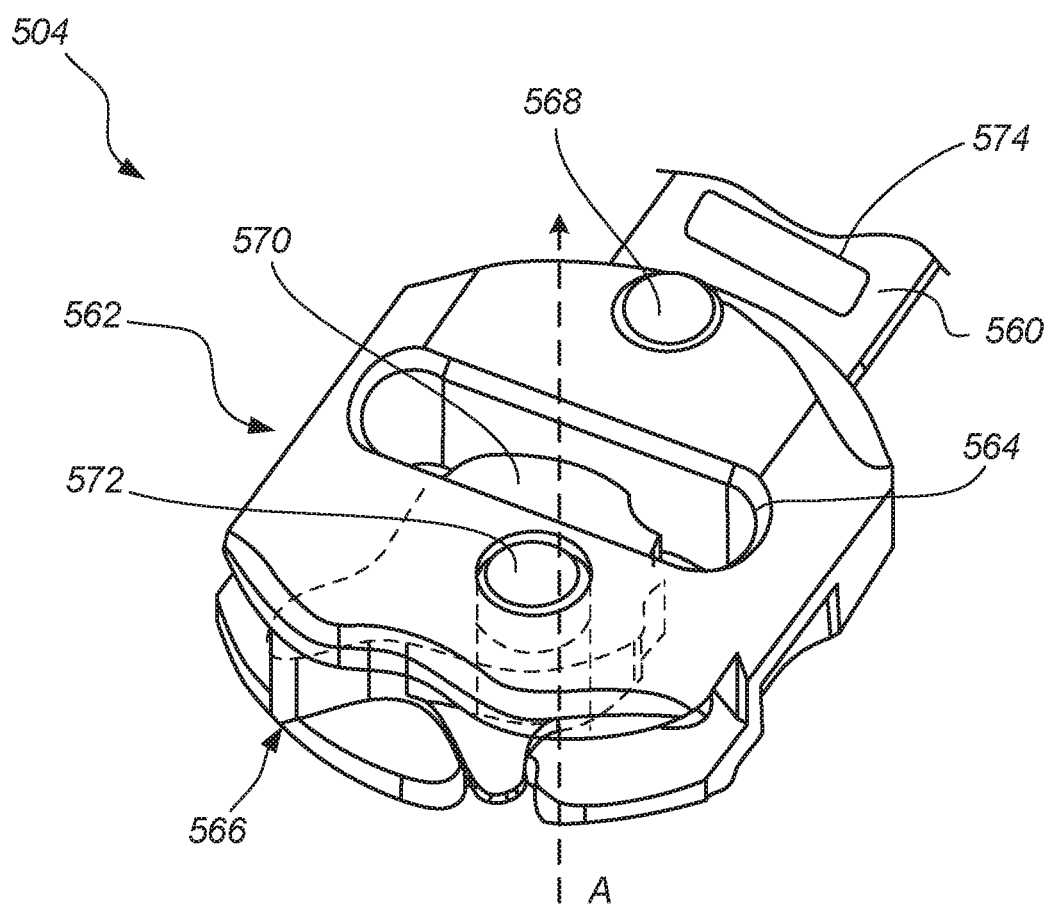
FIG. 6 illustrates an isometric view of a portion of a bar support, in accordance with at least one example of the present disclosure.

FIG. 6 illustrates an isometric view of a portion of bar support 504, according to at least one example of the present disclosure. Bar support 504 can include band 560 and fastener 562. Fastener 562 can include aperture 564, cam 566, and band pin 568. Cam 566 can include catch 570 and cam pin 572. Also shown in FIG. 6 is arrow A.

Aperture 564 can be a slot or opening passing through a body of fastener 562 sized to receive band 560. Pin 568 can be a pin insertable to the body of fastener 562 to secure one end of band 560 to fastener 562. In some examples, fastener 562 can be other types of fasteners, such as screws, and the like. Cam 566 can be a rotatable component coupled to the body of fastener 562 by cam pin 572. Cam catch 570 can be a portion of cam 566 that is actuatable into and out of aperture 564 and can be configured to engage a portion of band 560.

In operation of some examples, band 560 can be wrapped around ribs, as described in FIG. 5 above, and can be inserted into aperture 564 in the direction of arrow A. Cam 566 can then be actuated about cam pin 572 to so that catch 570 can engage band 560. Because band 560 can include slots 574 (one shown in FIG. 6), catch 572 can engage one of slots 574 to retain band 560 in aperture 564. In some other examples, catch 570 (or another portion of cam 566) can compress a portion of band 560 (against aperture 564) to retain band 560 within aperture 564. In some examples, cam 566 can be reversibly actuatable, so that catch 570 can disengage band 560 and band 560 can be removed from aperture 564 or inserted further through aperture 564 (in the direction of arrow A).

In these ways, fastener 562 allows for bar support 504 to be efficiently placed and secured during a procedure, and in some examples, quickly adjusted and/or removed. Bar support 504 offers several additional benefits. For example, because bar support 504 uses fastener 562 and is otherwise predominantly flat, bar support 504 has a low profile once installed and therefore may have a relatively low palpability. The flat profile of band 560 can also lower stress applied to the ribs, because the forces applied to a band may be distributed over a larger surface area of the ribs than a suture, for example. Because fastener 562 can hold band 560 rigidly, as compared to the prior art (a knot of a suture, for example), bar support 504 is less likely to slip under load.

Bar support 504 can be relatively stronger than pectus bar supports in the prior art, because it can be comprised of a semi-rigid metallic (for example, titanium) band. Also, because a band can be used instead of a needle and sutures, bar support 504 reduces a likelihood of injury to physicians.

Figure 7:
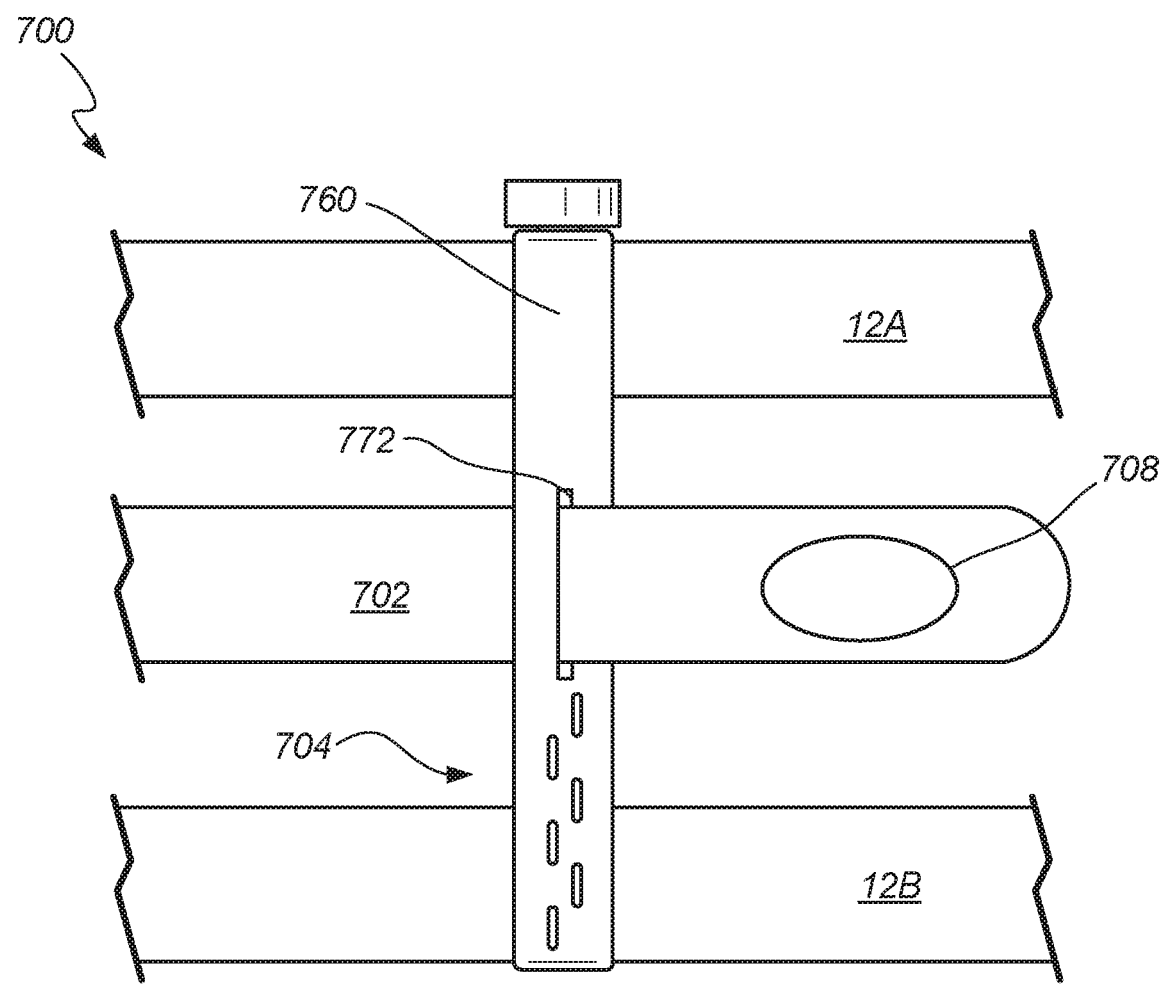
FIG. 7 illustrates an elevation view of a pectus bar assembly, in accordance with at least one example of the present disclosure.

FIG. 7 illustrates an elevation view of pectus bar assembly 700, which is another example of a pectus bar assembly in accordance with the present disclosure. Pectus bar assembly 700 can include pectus bar 702 and bar support 704. Bar support 704 can include a fastener (not shown), band 760, and slot 772. FIG. 7 also shows first rib 12A and second rib 12B.

Pectus bar 702 and bar support 704 can be similar to pectus bar 502 and bar support 504 of pectus bar assembly 500 shown in FIGS. 5 and 6 above. However, bar support 704 can include slot 772. Slot 772 can be a slot or opening in band 760 that is sized to receive pectus bar 702 therethrough. Because pectus bar 702 passes through band 760, band 760 can provide support to an anterior portion, a posterior portion, a superior portion, and an inferior portion of pectus bar 702, In other words, band 760 can support pectus bar 702 in all directions, which can provide the benefit of preventing undesired movement of pectus bar 702 within or relative to a ribcage of a patient in which pectus bar assembly 700 is installed.

Figure 8:
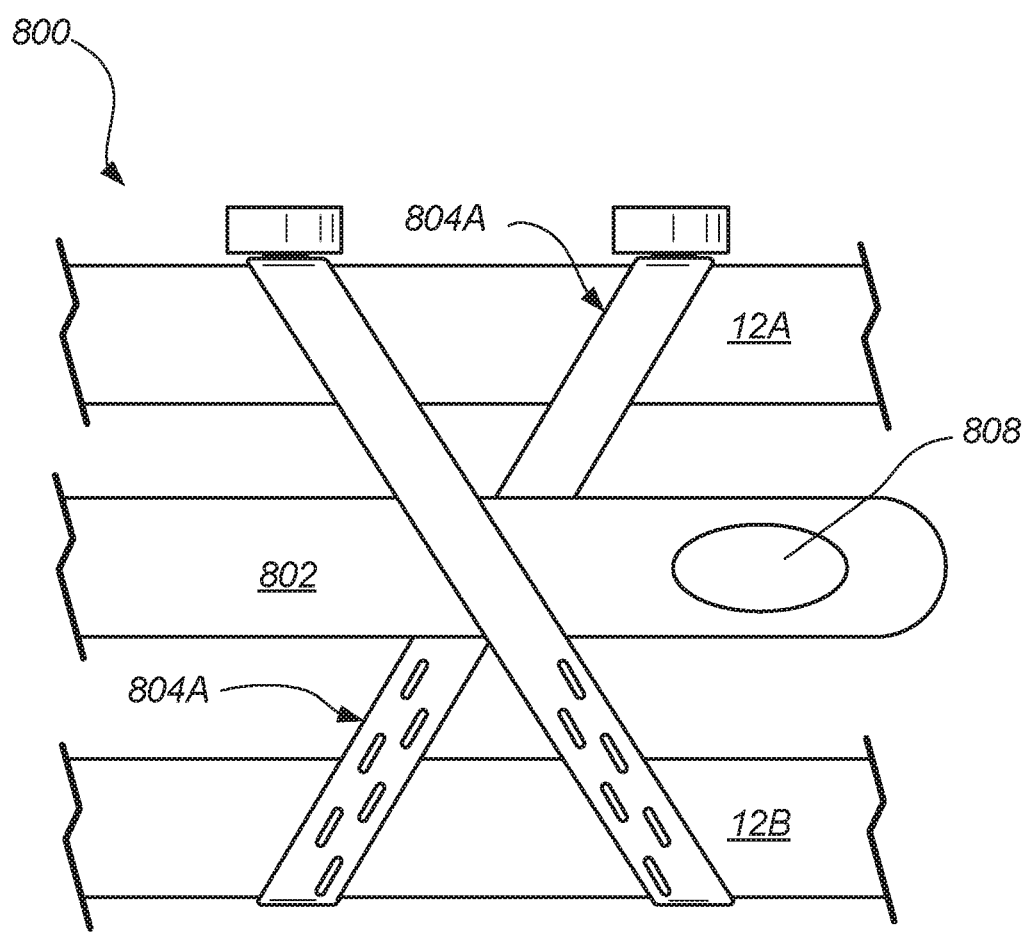
FIG. 8 illustrates an elevation view of a pectus bar assembly, in accordance with at least one example of the present disclosure.

FIG. 8 illustrates an elevation view of pectus bar assembly 800, which is another example of a pectus bar assembly in accordance with the present disclosure. Pectus bar assembly 800 can include pectus bar 802, bar support 804A, and bar support 804B. Each of bar supports 804A and 804B can include a fastener (not shown) and a band. FIG. 7 also shows first rib 12A and second rib 12B.

Pectus bar 802 and bar support 804 can be similar to pectus bar assemblies 500 and 700 discussed above. However, pectus bar assembly 800 can differ in that pectus bar assembly 800 can include two bar supports, bar supports 804A and 804B. In some examples, bar support 804A can encircle both of ribs 12A and 12B and can pass over a posterior portion of pectus bar 802 and bar support 804B can encircle both of ribs 12A and 12B and can pass over an anterior portion of pectus bar 802. In some examples, bar supports 804A and 804B can form an X-shape relative to each other. In some other examples, bar supports 804A and 804B may be placed in parallel to each other in supporting opposing sides of pectus bar 802. Though only two bar supports are shown in FIG. 8 more than two bar supports may be used in the same area to support pectus bar 802, such as 3, 4, 5, 6, 7, 8, 10, and the like.

By supporting anterior and posterior portions of pectus bar 802, bar supports 804A and 804B can provide the benefit of preventing undesired anterior and posterior movement of pectus bar 702 within a ribcage of a patient, following installation of these components.

In the various examples described herein, each bar support can be used, in the alternative (and in some cases together), to support the pectus bar 102 of FIG. 1 to correct pectus excavatum.

Figure 9:
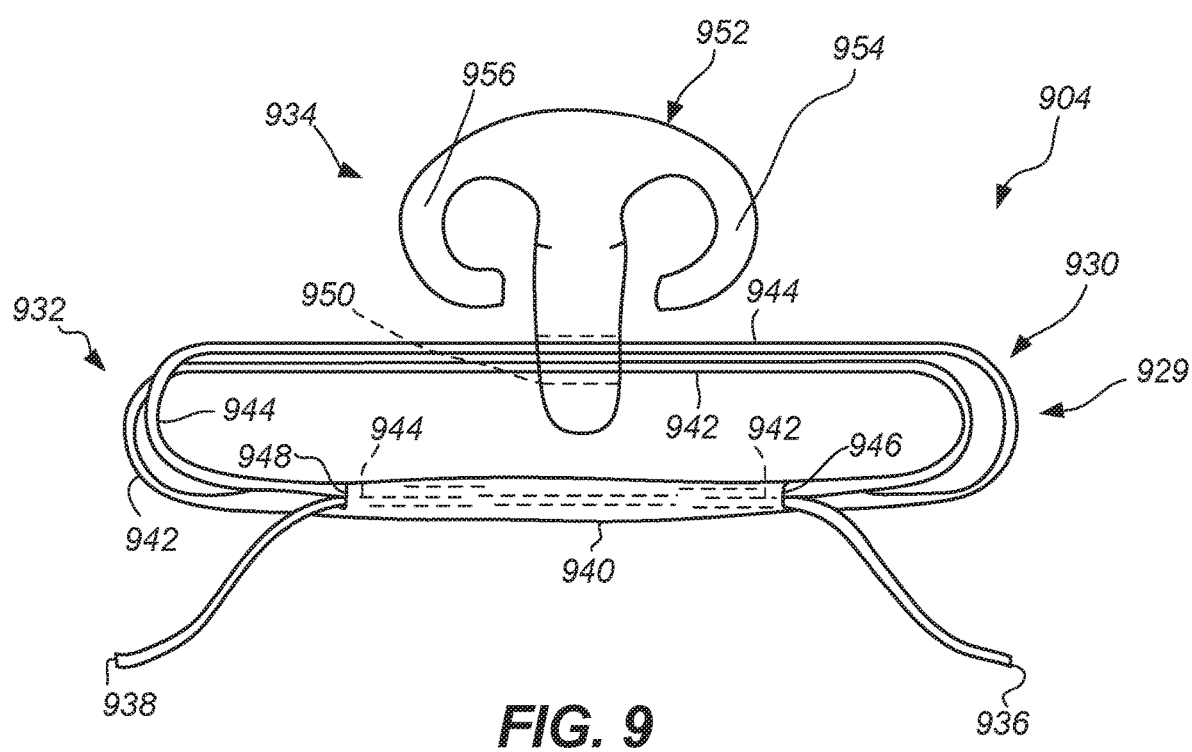
FIG. 9 illustrates a plan view of a bar support, in accordance with at least one example of the present disclosure.

FIG. 9 illustrates plan view of bar support 904, according to at least one example of the present disclosure. Bar support 904 can include loop portion 929 and coupler 934. Loop portion 929 can include first portion 930, second portion 932, first free end 936, second free end 938, sleeve 940, strand 942, and strand 944. Sleeve 940 can include first opening 946 and second opening 948. Coupler 934 can include channel 950 and open end 952. Open end 952 can include first hook 954 and second hook 956.

Strand 942 and strand 944 can be connected to each other and connected to sleeve 940. Sleeve 940 can be a pocket or enclosure integral to loop portion 929 together with first strand 942 and second strand 3944. Sleeve 940 can include first opening 946 proximate first portion 930 and second opening 948 proximate second portion 932. Sleeve 940 can be sized to receive one or more passes of both of strand 942 and strand 944, as discussed further below.

Coupler 934 can be a rigid coupler or fastener comprised of biocompatible materials, as described above. Coupler 934 can have a generally double-J-hook geometry with J-hooks facing substantially away from each other. Coupler 934 can include channel 950, which can be a passage or aperture disposed at the long portion of coupler 934 (or the closed portion), in some examples. Open end 952 of coupler 934 can include first hook 954 and second hook 956, each having an opening facing channel 950 and each being closed at a portion distal from channel 950. In other examples, coupler 934 can have other geometric shapes, such as a single J-hook, or coupler 934 can include a clasping device, such as a shackle or pivoting latch.

In assembly of one example of bar support 904, strand 942 can loop from second portion 932 through channel 950 of coupler 934 to first portion 930, through first opening 946, through sleeve 940, and out second opening 948, terminating as second free end 938. Similarly, strand 944 can loop from first portion 930 through channel 950 of coupler 934 to second portion 932, through second opening 948, through sleeve 940, and out first opening 946, terminating as first free end 936. This assembly can be performed at a factory, or prior to a surgical procedure, to save time and cost.

Once bar support 904 is assembled as shown in FIG. 9, bar support 904 can be installed on ribs, as described above, where coupler 934 is moved to second portion 932 and is placed to encircle a second rib. First portion 930, either before or after coupler 934 and second portion encircle the second rib, can be placed to encircle a first rib. Then, both of or each of strands 942 and 944 can be inserted into the openings of open end 952 into first hook 954 and second hook 956, respectively. Once strands 942 and 944 are installed in coupler 934, first free end and/or second free end can be pulled to tighten bar support 904 around the ribs, creating a support for a pectus bar. If desired, bar support 904 can be loosened and moved along the ribs, or can be removed and installed in another location, such as between two different ribs.

Bar support 904 can be quickly removed by cutting of either or both of strands 942 and 944. Because bar support 904 can be quickly installed, adjusted, and removed, bar support 304 can save time and cost in a procedure to install a pectus bar. Also, because strands 942 and 944 can be comprised of a relatively thin material, bar support 904 can lay relatively flat on ribs 12A and 12B, which can reduce palpability and can reduce irritation of surrounding tissues.

Figure 10:
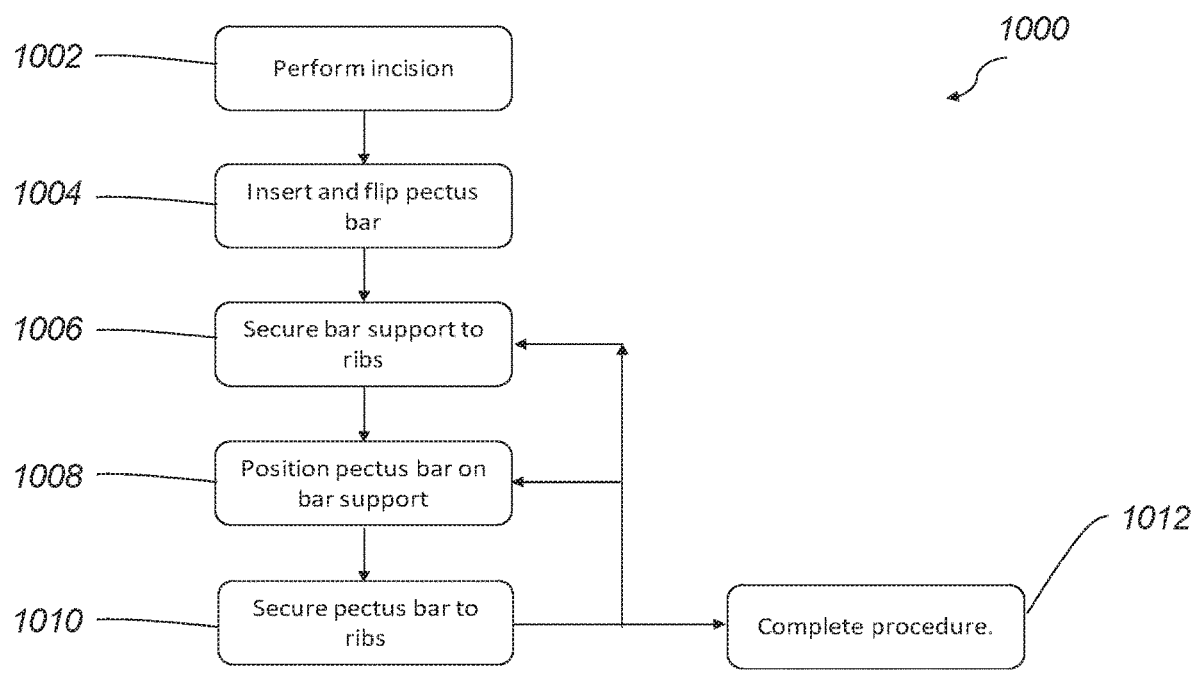
FIG. 10 illustrates a schematic view of a method, in accordance with at least one example of the present disclosure.

FIG. 10 shows a flow chart of using the devices and systems described above, in accordance with at least one example of this disclosure. The steps or operations of the method of FIG. 10 are illustrated in a particular order for convenience and clarity. Many of the discussed operations can be performed in a different sequence or in parallel, and some operations may be excluded, without materially impacting other operations. The method of FIG. 10, as discussed, includes operations that may be performed by multiple different actors, devices, and/or systems. It is understood that subsets of the operations discussed in the method of FIG. 10 that are attributable to a single actor, device, or system could be considered a separate standalone process or method.

In operation of one example, a physician can create one or more incisions on a ribcage of a patient at step 1002. Other preparations can be made at step 1002, such as detachment of soft tissues and resection of ribs, in some examples. At step 1004, a pectus bar, such as pectus bar 102, can be inserted into the ribcage and woven through one or more ribs and/or cartilage of the patient. Once fully inserted, the pectus bar can be flipped into an orientation that supports a proper rib cage shape or configuration. At any point after step 1004 and prior to step 1014, the pectus bar can be directly secured to the patient's rib cage using sutures and/or fasteners, as necessary, passing through a bore of the pectus bar.

At step 1006, a bar support, such as bar support 104 of FIG. 2, can be attached to ribs. Specifically, the bar support can be placed to encircle a first rib and placed to encircle a second rib that is adjacent to the first rib. The bar support can then be tightened, as desired, and secured to itself, for example, using one or more fasteners.

At step 1008, the pectus bar can be positioned to be supported by the bar support. If not already completed, the pectus bar can be secured to the ribs at step 1010. Following step 1010, if necessary, the bar support can be loosened or removed and can be repositioned on the pectus bar. Accordingly steps 1006 through 1012 can be repeated as necessary to position the bar support to appropriate support the pectus bar. Also, if necessary, additional bar supports may be installed on ribs to support the pectus bar and steps 1006 through 1010 can be completed as necessary for each bar support. Also, in some examples, steps 1002 through 1010 can be repeated for the installation of additional pectus bars. In some of these examples, only steps 1004 through 1010 may be used.

Once the bar support is locked to the pectus bar at a desired location, the procedure can be completed at step 1012, which can include connecting soft tissues, such as muscles, ligaments, cartilage, tendons to bones and to each other, and can include closing the incision or incisions.

Additional Notes

The above detailed description includes references to the accompanying drawings, which form a part of the detailed description. The drawings show, by way of illustration, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." in this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The invention claimed is:

1. A method for implanting a pectus bar support, the pectus bar support including a fastener secured to a to a first free end of a flexible member, the pectus bar support configured to support a pectus bar between a first rib and a second rib of a human ribcage, the method comprising:
   encircling, at least partially, a first rib and a second rib with the flexible member to support the pectus bar between the first rib and the second rib;
   tensioning the flexible member around the first rib and the second rib; and
   securing a second free end of the flexible member to the fastener.

2. The method of claim 1, further comprising:
   providing or obtaining a base; and
   providing or obtaining an insert.

3. The method of claim 2, further comprising;
coupling the insert to the base; and
securing the flexible member to the fastener by contacting the first free end and the second free end with the insert and the base when the insert is coupled to the base.

4. The method of claim 3, further comprising:
receiving the flexible member in a bore defined by the base.

5. The method of claim 4, further comprising:
threadably engaging the insert into a threaded surface defined by an extension of the base, wherein the extension extends inward from a wall of the bore.

6. The method of claim 5, further comprising:
passing the first free end and the second free end through a slot that extends through a periphery of the base and intersects the bore; and
passing the first free end and the second free end from the slot into the bore.

7. The pectus bar support of claim 4, wherein the flexible member is comprised of fabric having a width that is smaller than a diameter of the bore of the base.

8. The pectus bar support of claim 1, wherein the flexible member is comprised of fabric.

9. The pectus bar support of claim 1, wherein the flexible member is comprised of at least one of polyethylene, polyester, polyamide, a titanium alloy, and a stainless-steel alloy.

10. A method for implanting a pectus bar support, the pectus bar support configured to support a pectus bar between a first rib and a second rib of a human ribcage, the method comprising:
providing or obtaining a pectus bar support including a first portion including a first free end and a second portion including a second free end;
encircling, at least partially, a first rib of a ribcage with the first portion;
connecting the first portion to the second portion;
encircling, at least partially, a second rib of the ribcage adjacent to the first rib; and
adjusting tension of the first portion and the second portion around the first rib and the second rib, respectively, using one or more of the first free end and the second free end.

11. The method of claim 10, further comprising:
securing a connector to the first portion and the second portion.

12. The method of claim 11, further comprising:
releasably coupling the first portion to the connector.

13. The method of claim 11, further comprising:
releasably securing an open end of the first portion to the connector.

14. The method of claim 10, wherein the pectus bar support comprises a sleeve coupled to the first portion and the second portion, the first free end and the second free end passing through the sleeve to create at least one loop.

15. The method of claim 14, farther comprising:
securing a connector of the pectus bar support to the first portion and the second portion.

16. The method of claim 15, further comprising:
releasably securing an open end of the connector to the second portion.

17. A method for implanting a pectus bar support, the pectus bar support configured to support a pectus bar between a first rib and a second rib of a human ribcage, the method comprising:
encircling, at least partially, a first end of a band around a first rib of a ribcage and a second end of the band around a second rib of the ribcage;
releasably securing a fastener secured to the second end of the band to the first end of the band; and
tensioning the band around the first rib and the second rib using the fastener.

18. The method of claim 17, wherein the fastener comprises a buckle extending from the second end.

19. The method of claim 18, further comprising:
receiving the first end in an aperture of the buckle; and
rotating a cam within the buckle to secure the first end to the buckle.

20. The method of claim 19, further comprising:
receiving the cam in a slot of the band to secure the band to the buckle.

* * * * *